United States Patent [19]
Grayson

[11] 4,429,131
[45] Jan. 31, 1984

[54] PROCESS FOR THE PRODUCTION OF 3,5-DIALKYLPYRIDINES

[75] Inventor: James I. Grayson, Visp, Switzerland

[73] Assignee: Lonza Ltd., Gampel, Switzerland

[21] Appl. No.: 396,102

[22] Filed: Jul. 7, 1982

[30] Foreign Application Priority Data

Jul. 9, 1981 [CH] Switzerland ............... 4504/81

[51] Int. Cl.$^3$ .............................................. C07D 213/09
[52] U.S. Cl. ............................. 546/251; 252/188.31
[58] Field of Search ......................................... 546/251

[56] References Cited

U.S. PATENT DOCUMENTS 4,337,342 6/1982 Dinkel .............................. 546/251

FOREIGN PATENT DOCUMENTS 2123965 11/1972 Fed. Rep. of Germany ...... 546/251
1332908  6/1963 France ............................... 546/251

Primary Examiner—Robert T. Bond
Attorney, Agent, or Firm—Fisher, Christen & Sabol

[57] ABSTRACT

Process for the production of 3,5-dialkylpyridines. An aldehyde having the formula R—CH$_2$—CHO, wherein R is a straight-chained or branched alkyl radical having 1 to 6 carbon atoms, and/or an acetal of such aldehyde is reacted with formaldehyde and/or hexamethylene tetramine and/or a formaldehyde acetal and/or a polymer of formaldehyde in liquid or aqueous phase at a temperature of 180° to 280° C. in a closed vessel in the presence of ammonia and/or ammonium ions and in the presence of anions of an inorganic and/or an organic acid, both of which at 20° C. have an acid dissociation constant of $10^6$ to $10^{-12}$.

20 Claims, No Drawings

PROCESS FOR THE PRODUCTION OF 3,5-DIALKYLPYRIDINES

BACKGROUND OF THIS INVENTION

1. Field of this Invention

This invention relates to a process for the production of 3,5-dialkylpyridines.

2. Prior Art 3,5-dialkylpyridines are important intermediate products in the chemical industry, for example, in the production of plant preservatives or dinicotinic acid. Various processes for the production of 3,5-dialkylpyridines are known.

3,5-dialkylpyridines have been produced in a gas phase reaction from formaldehyde, ammonia and an aliphatic aldehyde of the formula R—$CH_2$—CHO (see French Patent No. 1,332,908). Thus, from formaldehyde, n-butyraldehyde and ammonia, 3,5-diethylpyridine was obtained at 400° C. on an aluminum silicate catalyst impregnated with lead fluoride. The yield corresponded to a conversion of 50 percent. Analogously 3,5-dimethylpyridine was obtained from formaldehyde, propionaldehyde and ammonia solution. Such a process has not attained any technical importance. The necessity of having to always regenerate the catalyst in oxygen or in a stream of air is a serious disadvantage. Due to the required high temperatures, a pitchlike material and its decomposition products are formed—they cause coking of the apparatus and catalyst and make the separation of the desired 3,5-dialkylpyridine difficult.

According to German OS No. 2,123,965 a precondensate of formaldehyde and an aldehyde R—$CH_2$—CHO is formed in the first step of a two-step fluid phase process. Subsequently the precondensate is transformed into 3,5-dialkylpyridine in a second step with ammonia and/or ammonium salts at 200° to 300° C. over 8 to 10 hours. The yields lie between 11 and 46 percent. The disadvantage of such a process is that it has two steps and requires long reaction times.

BROAD DESCRIPTION OF THIS INVENTION

An object of this invention is to provide a process for the production of 3,5-dialkylpyridine in short reaction times with high yields. Another object of this invention is to provide certain compositions. Other objects and advantages of this invention are set out herein or are obvious herefrom to one ordinarily skilled in the art.

The objects and advantages of this invention are achieved by the process of this invention.

This invention includes a process for the production of 3,5-dialkylpyridines. The process includes reacting, in mixture form, an aldehyde having the formula R—$CH_2$—CHO, wherein R is a straight-chained or branched alkyl radical having 1 to 6 carbon atoms, and/or an acetal of such aldehyde with formaldehyde and/or hexamethylene tetramine and/or a formaldehyde acetal and/or a polymer of formaldehyde in liquid or aqueous phase at a temperature of 180° to 280° C. in a closed vessel in the presence of ammonia and/or ammonium ions and in the presence of anions of an inorganic and/or an organic acid, both of which at 20° C. have an acid dissociation constant of $10^6$ to $10^{-12}$.

A molar ratio of aldehyde having the formula R—$CH_2$—CHO to formaldehyde and/or hexamethylene tetramine and/or a formaldehyde acetal is preferably from 1 to 0.5 to 1 to 1.5. Preferably the anions of the inorganic and/or organic acids are inserted into the reaction solution by addition of the corresponding water-soluble alkali and/or ammonium salts. The ammonium salts preferably are used in an aqueous solution in a concentration of 0.3 to 10 mole/l. Also, preferably the process is operated at a temperature of 205° to 240° C. The aldehydes having the formula R—$CH_2$—CHO can be used in the form of their acetals.

This invention also includes a composition composed of (a) an aldehyde having the formula R—$CH_2$—CHO, wherein R is a straight-chained or branched alkyl radical having 1 to 6 carbon atoms, and/or an acetal of such aldehyde (b) formaldehyde and/or hexamethylene tetramine and/or a formaldehyde acetal, and/or a polymer of formaldehyde (c) ammonia and/or ammonium ions and (d) anions of an inorganic acid and/or an organic acid, both of which at 20° C. have an acid dissociation constant of $10^6$ to $10^{-12}$.

DETAILED DESCRIPTION OF THIS INVENTION

The phrase "aldehydes having the formula R—$CH_2$—CHO", as used herein, includes the acetals thereof, for example, propionaldehyde diethyl acetal. The term formaldehyde, as used herein, includes its acetals, for example, formaldehyde dimethyl acetal, and its polymers, for example, trioxane.

In order to insert the anions (which are important for the reaction) of the inorganic and/or organic acids (which at 20° C. have an acid dissociation constant of $10^6$ to $10^{-12}$) into the reaction solution, the corresponding water-soluble alkali and/or ammonium salt of the acids are added to the reaction solution. The salts of the acids useful in this invention are, for example, the sodium, potassium or ammonium salts of pentaboric acid, such as, ammonium pentaborate, of carbonic acid, such as, ammonium carbonate, of phosphoric acid, such as, potassium dihydrogen phosphate, ammonium dihydrogen phosphate, dipotassium hydrogen phosphate or diammonium hydrogen phosphate, of sulfuric acid, such as, sodium hydrogen sulfate or ammonium sulfate, of hydrofluoric acid, such as, sodium fluoride, ammonium fluoride or ammonium hydrogen difluoride, of hydrochloric acid, such as, ammonium chloride, of hydrogen bromide, such as, ammonium bromide, of heptamolybdic acid, such as, ammonium heptamolybdate, of formic acid, such as, ammonium formate, of acetic acid, such as, sodium acetate or ammonium acetate, of propionic acid, such as, ammonium propionate, of butyric acid, such as, ammonium butyrate, of succinic acid, such as, disodium succinate or diammonium succinate, of adipic acid, such as, diammonium adipinate, of benzoic acid, such as, sodium benzoate or ammonium benzoate, of phthalic acid, such as, diammonium phthalate, of terphthalic acid, such as, diammonium terphthalate, of nicotinic acid, such as ammonium nicotinate, and of isonicotinic acid, such as, ammonium isonicotinate.

For the formation of 3,5-dialkylpyridine from an aldehyde having the formula R—$CH_2$—CHO in a mixture with formaldehyde, the presence of ammonia and/or ammonium ions is necessary. Whenever ammonia is used, which can be used either in a gaseous form or as an aqueous solution, it is sufficient if alkali salts of the cited acids are used. However, mixtures of alkali salts and ammonium salts can also be used. If one does without the ammonia (i.e., as a gas or as an aqueous ammonia solution), then an ammonium salt or salts, or a mixture of ammonium salt(s) and alkali salt(s) are used.

Whenever liquid starting materials, which are not intermiscible, are used together with aqueous formaldehyde, then it is advantageous to use small quantities of homogenizing agents, such as, alcohols or cyclic ethers, for the homogenization. Examples of such alcohols are alkanols having 1 to 5 carbon atoms, such as, ethanol. Examples of such cyclic ethers are tetrahydrofurane.

The process of this invention is carried out effectively with a molar ratio of aldehyde to formaldehyde and/or hexamethylenetetramine and/or formaldehydeacetal of 1 to 0.5 to 1 to 1.5, preferably of 1 to 0.8 to 1 to 1.2. The reaction temperature advantageously is 180° to 280° C., effectively is 205° to 240° C. and preferably is 225° to 235° C. The reaction is carried out in the liquid phase (aqueous phase) under a pressure which occurs in the case of the reaction in the closed vessel at the predetermined temperature. It is advantageous to stir the reaction batch during the reaction. The quantity of ammonia and/or ammonium ions used in 0.5 to 3 mole of ammonia and/or ammonium ions per mole of aldehyde, and is effectively 0.5 to 2.0 mole per mole of aldehyde. The quantity of the anions of the inorganic and/or organic acids used is effectively 0.1 to 3 moles, preferably 0.2 to 1.0 mole, per mole of aldehyde. The starting pH value of the aqueous reaction solution is effectively between 5.0 and 12.5.

The addition of the aldehyde is accomplished effectively according to the measure of its consumption. Thus it is advantageous, for example, in the case of working in a 2-liter container and with the use of 350 ml of aldehyde to add the latter continuously during a 30 to 90 minute period. In the case of other conditions, corresponding addition times are to be selected.

At the end of the desired reaction period, the temperature is lowered to approximately ambient temperature and 3,5-dialkylpyridine is obtained from the reaction mixture in a known manner. One recovery method is based on first bringing the pH value of the water phase into the basic range and then extracting the organic material from the aqueous reaction mixture with an organic solvent, such as, benzene, toluene, xylene, methylene chloride, chloroform, ether, etc. The organic solvent is then evaporated and 3,5-dialkylpyridine is obtained by fractional distillation. Within the scope of this invention, any other desirable or useful methods for separating and obtaining the product can also be used.

One advantage of the process according to this invention is also that the aqueous phase obtained after the extraction of the reaction mixture with an organic solvent can be returned to the reactor after reenrichment with ammonia and/or ammonium ions. The aqueous salt phase is composed of the originally present quantity of water in the salt solution, the unreacted quantity of ammonia and/or ammonium salt, the optionally present metal salt, the liberated acid of the ammonium salt participating in the reaction, and one mole of water for every mole of aldehyde consumed during the reaction. The aqueous salt phase, therefore, is concentrated with the help of any known useful process, for example, by evaporation, in order to remove the water which formed as a consequence of the condensation reaction. A reenrichment of ammonia and/or ammonium salt can be achieved by introducing gaseous ammonia at ambient temperature into the aqueous solution with reformation of the ammonium salt from the optionally present acid.

Although this invention has been described as a batch discontinuous process, such process can also be operated continuously within the scope of this invention. In the case of the continuous process embodiment, the reaction participants are introduced continuously into a suitable pressure reactor from which the reaction mixture is continuously drawn off. The reaction products are separated from the reaction mixture, the aqueous salt phase is reconcentrated and unchanged reaction participants are supplemented again and returned to the reaction vessel. The continuous process can be carried out in any reaction which permits an intimate intermixing of the reaction participants while stirring vigorously, for example, in a continuously-stirred tank reactor.

By way of summary, this invention involves a process for the production of 3,5-dialkylpyridine from a mixture of an aldehyde having the formula $R-CH_2-CHO$ and formaldehyde in the liquid phase.

As used herein, all percentages, ratios, parts and proportions are on a weight basis unless otherwise stated herein or otherwise obvious herefrom to one ordinarily skilled in the art.

EXAMPLE 1

1140 ml of a 3.40 molar aqueous solution of diammonium hydrogen phosphate (pH 8.3) was heated in a 2-liter autoclave to 230° C. and was then stirred at 1500 rpm. Within 62 minutes, a mixture of 127.6 of propionaldehyde, 213.3 g of a 30.2 percent formaldehyde solution and 50.0 g of ethanol was continuously pumped into this solution (molar ratio of propionaldehyde to formaldehyde = 1 to 1). At the same time the reaction pressure varied between 31 and 42 bar. After completion of the addition of the educt mixture, the reaction mass continued to be stirred for 10 minutes at 230° C. and was then cooled to ambient temperature. An extraction was made 3 times with 100 ml of methylene chloride, and a gas chromatographic analysis was made of the combined methylene chloride extracts. The yield of 3,5-lutidiene was 46.1 percent, based on the amount of propionaldehyde used.

All of the gas chromatographic analyses in the examples were carried out with the use of an internal standard as well as with due regard to the surface correction factors.

EXAMPLE 2

1140 ml of a 3.40 molar aqueous solution of diammonium hydrogen phosphate (pH 8.3) was heated in a 2-liter autoclave at 210° C. and was then stirred at 1500 rpm. Into this solution, a mixture of 127.6 g of propionaldehyde, 213.3 g of a 30.2 percent formaldehyde solution and 50.0 g of ethanol was continuously pumped within a 56 minute period (molar ratio of propionaldehyde to formaldehyde = 1 to 1). At the same time the reaction pressure varied between 21 and 30 bar. After completion of the addition of the educt mixture, the reaction mass continued to be stirred for 10 minutes at 210° C. and was then cooled to ambient temperature. An extraction was made 3 times with 100 ml of methylene chloride, and a gas chromatographic analysis was made of the combined extracts. The yields of 3,5-lutidine was 38.3 percent, based on the amount of propionaldehyde used.

EXAMPLE 3

1140 ml of a 3.40 molar aqueous solution of diammonium hydrogen phosphate (pH 8.3) was heated in a 2-liter autoclave to 232° C. and was then stirred at 1500 rpm. A mixture of 148.7 g of butyraldehyde, 201.0 g of a 30.2 percent formaldehyde solution and 70.0 g of ethanol was continuously pumped into this solution within a 58 minute period (molar ratio of butyraldehyde to formaldehyde = 1 to 1). At the same time the reaction pressure varied between 33 and 47 bar. After completion of the addition of the educt mixture, the reaction mass continued to be stirred for 20 minutes at 232° C. and was then cooled to ambient temperature. An extraction was made 3 times with 100 ml of methylene chloride, and a gas chromatographic analysis was made of the combined methylene extracts. The yield of 3,5-diethylpyridine was 55.0 percent, based on the amount of butyraldehyde used.

EXAMPLE 4

1140 ml of a 3.40 molar aqueous solution of diammonium hydrogen phosphate (pH 8.3) was heated in a 2-liter autoclave to 210° C. and was then stirred at 1500 rpm. Within 55 minutes, a mixture of 148.7 g of butyraldehyde, 200.5 g of a 30.3 percent formaldehyde solution and 59.0 g of ethanol was continuously pumped into this solution (molar ratio of butyraldehyde to formaldehyde = 1 to 1). At the same time the reaction pressure varied between 21 and 33 bar. After completion of the addition of the educt mixture, the reaction mass continued to be stirred for 10 minutes at 210° C. and was then cooled to ambient temperature. An extraction was made 3 times with 100 ml of methylene chloride and a gas chromatographic analysis was made of the combined methylene chloride extracts. The yield of 3,5-diethylpyridine was 47.1 percent, based on the amount of butyraldehyde used.

EXAMPLE 5

1140 ml of a 3.40 molar aqueous solution of diammonium hydrogen phosphate (pH 8.3) was heated to 232° C. in a 2-liter autoclave and was then stirred at 1500 rpm. A mixture of 148.7 g of butyraldehyde, 47.9 g of hexamethylene tetramine, 120 g of water and 110 g of ethanol was continuously pumped into this solution within a 58 minute period (calculated molar ratio of butyraldehyde to formaldehyde = 1 to 1). At the same time the reaction pressure varied between 32 an 58 bar. After completion of the addition of the educt mixture, the reaction mass continued to be stirred at 232° C. for 20 minutes and was then cooled to ambient temperature. An extraction was made 3 times with 100 ml of methylene chloride, and a gas chromatographic analysis was made of the combined methylene chloride extracts. The yield of 3,5-diethylpyridine was 49.0 percent based on the amount of butyraldehyde used.

EXAMPLE 6

1140 ml of a 3.40 molar aqueous solution of ammonium acetate (pH 7.7) was heated in a 2-liter autoclave to 232° C. and was then stirred at 1500 rpm. A mixture of 127.6 g of propionaldehyde, 213.3 g of a 30.3 percent formaldehyde solution and 50.0 g of ethanol was continuously pumped into this solution within a 57 minute period (molar ratio of propionaldehyde to formaldehyde = 1 to 1). At the same time the reaction pressure varied between 26 and 34 bar. After completion of the addition of the educt mixture, the reaction mass continued to be stirred for 10 minutes at 232° C. and was then cooled to ambient temperature. An extraction was made 3 times with 100 ml of methylene chloride, and a gas chromatographic analysis was made of the combined methylene chloride extracts. The yield of 3,5-lutidine was 44.2 percent, based on the amount of propionaldehyde used.

EXAMPLE 7

A solution of 397.1 g of dipotassium hydrogen phosphate in 1140 ml of 2.5 molar aqueous ammonia (pH 12.0) was heated to 232° C. in a 2-liter autoclave and was then stirred at 1500 rpm. A mixture of 127.6 g of propionaldehyde, 213.3 g of a 30.1 percent formaldehyde solution and 50.0 g of ethanol was continuously pumped into this solution within a 60 minute period (molar ratio of propionaldehyde to formaldehyde = 1 to 1). At the same time the reaction pressure varied between 33 and 35 bar. After completion of the addition of the educt mixture, the reaction mass continued to be stirred for 10 minutes at 232° C. and was then cooled to ambient temperature. An extraction was made 3 times with 100 ml of methylene chloride, and a gas chromatographic analysis was made of the combined methylene chloride extracts.

The yield of 3,5-lutidine was 28.8 percent, based on the amount of propionaldehyde used.

EXAMPLE 8

1140 ml of a 3.40 molar aqueous solution of diammonium hydrogen phosphate (pH 8.3) was heated in a 2-liter autoclave to 232° C. and was then stirred at 1500 rpm. A mixture of 140.0 g butyraldehyde and 153.0 g of formaldehyde dimethylacetal was continuously pumped into this solution within a 64 minute period (molar ratio of butyraldehyde to formaldehyde dimethylacetal = 1 to 1). At the same time the reaction pressure varied between 33 and 43 bar. After completion of the addition of the educt mixture, the reaction mass continued to be stirred for 20 minutes at 232° C. and was then cooled to ambient temperature. An extraction was made 3 times with 100 ml of methylene chloride, and a gas chromatographic analysis was made of the combined methylene chloride extracts. The yield of 3,5-diethylpyridine was 46.7 percent related to the amount of butyraldehyde used.

EXAMPLE 9

A solution of 137.0 g of sodium hydrogen sulfate monohydrate in 1140 ml of 4.0 molar aqueous ammonia (pH 10.8) was heated in a 2-liter autoclave to 232° C. and was then stirred at 1500 rpm. Within 64 minutes, a mixture of 140.0 g butyraldehyde and 153.0 g of formaldehyde dimethylacetal was continuously pumped into this solution (molar ratio of butyraldehyde to formaldehyde dimethylacetal = 1 to 1). At the same time the reaction pressure varied between 36 and 44 bar. After completion of the addition of the educt mixture, the reaction mass continued to be stirred for 20 minutes at 232° C. and was then cooled to ambient temperature. An extraction was made 3 times with 100 ml of methylene chloride, and a gas chromatographic analysis was made of the combined methylene chloride extracts. The yield of 3,5-diethylpyridine was 58.6 percent, based on the amount of butyraldehyde used.

EXAMPLE 10

1140 ml of a 3.40 molar aqueous solution of diammonium hydrogen phosphate (pH 8.3) was heated in a 2-liter autoclave to 232° C. and was then stirred at 1500 rpm. Into this solution, a mixture of 127.6 g of propionaldehyde, 179.0 g of a 30.1 percent formaldehyde solution and 50.0 g of ethanol was continuously pumped within a 74 minute period (molar ratio of propionaldehyde to formaldehyde=1.2 to 1). At the same time the reaction pressure varied between 33 and 40 bar. After completion of the addition of the educt mixture, the reaction mass continued to be stirred for 10 minutes at 232° C. and was then cooled to ambient temperature. An extraction was made 3 times with 100 ml of methylene chloride, and a gas chromatographic analysis was made of the combined methylene chloride extracts. The yield of 3,5-lutidine was 47.4 percent, based on the amount of propionaldehyde used.

EXAMPLE 11

1140 ml of a 3.40 molar aqueous solution of diammonium hydrogen phosphate (pH 8.3) was heated in a 2-liter autoclave to 232° C. and was then stirred at 1500 rpm. A mixture of 105.6 g of propionaldehyde, 213.3 g of a 30.1 percent formaldehyde solution and 50.0 g of ethanol was continuously pumped into this solution within a 62 minute period (molar ratio of propionaldehyde to formaldehyde=0.83 to 1). At the same time the reaction pressure varied between 33 and 47 bar. After completion of the addition of the educt mixture, the reaction mass continued to be stirred for 10 minutes at 232° C. and was then cooled to ambient temperature. An extraction was made 3 times with 100 ml of methylene chloride, and a gas chromatographic analysis was made of the combined methylene chloride extracts. The yield of 3,5-lutidine was 47.5 percent, based on the amount of propionaldehyde used.

EXAMPLE 12

1140 ml of a 3.40 molar aqueous solution of diammonium hydrogen phosphate (pH 8.3) was heated in a 2-liter autoclave to 232° C. and was then stirred at 1500 rpm. Into this solution, a mixture of 127.6 g of propionaldehyde, 143.6 g of a 30.1 percent formaldehyde solution and 50.0 g of ethanol was continuously pumped within a 63 minute period (molar ratio of propionaldehyde to formaldehyde=1.5 to 1). At the same time the reaction pressure varied between 33 and 39 bar. After completion of the addition of the educt mixture, the reaction mass continued to be stirred for 10 minutes at 232° C. and was then cooled to ambient temperature. An extraction was made 3 times with 100 ml of methylene chloride, and a gas chromatographic analysis was made of the combined methylene chloride extracts. The yield of 3,5-lutidine was 48.5 percent, based on the amount of propionaldehyde used.

EXAMPLE 13

1140 ml of a 3.40 molar aqueous solution of diammonium hydrogen phosphate (pH 8.3) was heated in a 2-liter autoclave to 230° C. and was then stirred at 1500 rpm. Into this solution, a mixture of 202.3 g of propionaldehydediethylacetal and 120.2 g of formaldehydedimethylacetal was continuously pumped within a 64 minute period (molar ratio of propionaldehydediethylacetal to formaldehydedimethylacetal=1 to 1). At the same time the reaction pressure varied between 32 and 46 bar. After completion of the addition of the educt mixture, the reaction mass continued to be stirred for 10 minutes at 230° C. and was then cooled to ambient temperature. An extraction was made 3 times with 100 ml of methylene chloride, and a gas chromatographic analysis was made of the combined methylene chloride extracts. The yield of 3,5-lutidine was 48.6 percent, based on the amount of propionaldehyde used.

EXAMPLE 14

1140 ml of a 3.40 molar aqueous solution of diammonium hydrogen phosphate (pH 8.3) was heated in a 2-liter autoclave to 230° C. and was then stirred at 1500 rpm. A mixture of 88.9 g of propionaldehyde, 46.0 g of trioxane, 100.0 g of water and 50.0 g of ethanol was continuously pumped into this solution (calculated molar ratio of propionaldehyde to formaldehyde=1 to 1). At the same time the reaction pressure varied between 32 and 37 bar. After completion of the addition of the educt mixture, the reaction mass continued to be stirred for 10 minutes at 230° C. and was then cooled to ambient temperature. An extraction was made 3 times with 100 ml of methylene chloride, and a gas chromatographic analysis was made of the combined methylene chloride extracts. The yield of 3,5-lutidine was 38.1 percent, based on the propionaldehyde used.

EXAMPLE 15

1140 ml of a 3.40 molar aqueous solution of diammonium hydrogen phosphate (pH 8.3) was heated in a 2-liter autoclave to 232° C. and was then stirred at 1500 rpm. A mixture of 150.7 g of isovaleraldehyde, 174.6 g of a 30.1 percent formaldehyde solution and 115 g of ethanol was continusouly pumped into this solution within a 63 minute period (molar ratio of isovaleraldehyde to formaldehyde=1 to 1). At the same time the reaction pressure varied between 32 and 49 bar. After completion of the addition of the educt mixture, the reaction mass continued to be stirred for 20 minutes at 232° C. and was then cooled to ambient temperature. An extraction was made 3 times with 100 ml of methylene chloride. The combined methylene chloride extracts from such three extractions were distilled, whereby 226.6 g of 3,5-diisopropylpyridine was obtained. The gas chromatographic analysis resulted in a content of 96.1 percent, which corresponded to a yield of 51.3 percent of 3,5-diisopropylpyridine.

EXAMPLE 16

1140 ml of a 3.40 molar aqueous solution of diammonium hydrogen phosphate (pH 8.3) were heated in a 2-liter autoclave to 232° C. and were stirred at 1500 rpm. Into this solution, a mixture of 151.0 g of capronaldehyde, 150.0 g of a 30.1 percent formaldehyde solution and 130.0 g of ethanol was continuously pumped within a 63 minute period (molar ratio of capronaldehyde to formaldehyde=1 to 1). At the same time the reaction pressure varied between 33 and 46 bar. After completion of the addition of the educt mixture, the reaction mass continued to be stirred for 30 minutes at 232° C. and was then cooled to ambient temperature. An extraction was made 3 times with 100 ml of methylene chloride. The combined methylene chloride extracts from such three extractions were distilled, whereby 217.3 g of 3,5-dibutylpyridine was obtained. The gas chromatographic analysis resulted in a content of 92.3 percent, which corresponds to a yield of 46.9 percent of 3,5-dibutylpyridine.

What is claimed is:

1. Process for the production of a 3,5-dialkylpyridine comprising reacting, in mixture form, (a) an aldehyde having the formula R—CH$_2$—CHO, wherein R is a straight-chained or branched alkyl radical having 1 to 6 carbon atoms, and/or an aldehyde acetal of said aldehyde with (b) formaldehyde and/or hexamethylene tetramine and/or a formaldehyde acetal and/or a polymer of formaldehyde in liquid or aqueous phase at a temperature of 180° to 280° C. in a closed vessel in the presence of ammonia and/or ammonium ions and in the presence of anions of a inorganic acid and/or an organic acid, both of which 20° C. have an acid dissociation constant of $10^6$ to $10^{-12}$.

2. Process as claimed in claim 1 wherein the aldehyde is an acetal thereof.

3. Process as claimed in claim 1 wherein the formaldehyde is a polymer thereof.

4. Process as claimed in claim 1 wherein the anions of the inorganic and/or organic acids are inserted into the reaction solution by addition of the corresponding water-soluble alkali and/or ammonium salts thereof.

5. Process as claimed in claim 4 wherein the water-soluble alkali salt is a sodium salt or a potassium salt.

6. Process as claimed in claim 1 wherein the salt is used in an aqueous solution in a concentration of 0.3 to 1.0 mole/l.

7. Process as claimed in claim 1 wherein the mole ratio of the aldehyde having the formula R—CH$_2$—CHO to the formaldehyde and/or hexamethylene tetramine and/or formaldehyde acetal is from 1 to 0.5 to 1 to 1.5.

8. Process as claimed in claim 7 wherein the molar ratio is from 1 to 0.8 to 1 to 1.2.

9. Process as claimed in claim 1 wherein, when formaldehyde is used, a small quantity of an alcohol or a cyclic ether is used as a homogenizing agent.

10. Process as claimed in claim 1 wherein the temperature is between 225° and 235° C.

11. Process as claimed in claim 1 wherein the temperature is between 205° and 240° C.

12. Process as claimed in claim 1 wherein the reaction mixture is stirred during the reaction.

13. Process as claimed in claim 1 wherein 0.5 to 3 moles of ammonia and/or ammonium ions are used per mole of aldehyde.

14. Process as claimed in claim 1 wherein 0.5 to 2.0 moles of ammonia and/or ammonium ions are used per mole of aldehyde.

15. Process as claimed in claim 1 wherein 0.1 to 3 moles of the anions of the inorganic and/or organic acids are used per mole of aldehyde.

16. Process as claimed in claim 1 wherein 0.2 to 1.0 of the anions of the inorganic and/or organic acids are used per mole of aldehyde.

17. Process as claimed in claim 1 wherein the pH of the aqueous reaction solution is between 5.0 and 12.5.

18. Process as claimed in claim 1 wherein the reaction is conducted on a continuous basis.

19. Process as claimed in claim 1 wherein the temperature of the reaction solution, after the reaction, is lowered to about room temperature, the pH of the aqueous phase reaction solution is made basic, the organic material in the aqueous phase is extracted with an organic solvent, the organic solvent is extracted and the 3,5-dialkylpyridine is obtained by fractional distillation.

20. Process as claimed in claim 19 wherein the aqueous phase, after extraction with the organic solvent and reenrichment with ammonia and/or ammonium ions is recycled or reused.

* * * * *